United States Patent
Avnery

(10) Patent No.: US 7,183,563 B2
(45) Date of Patent: *Feb. 27, 2007

(54) IRRADIATION APPARATUS

(75) Inventor: Tzvi Avnery, Winchester, MA (US)

(73) Assignee: Advanced Electron Beams, Inc., Wilmington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/796,796

(22) Filed: Mar. 8, 2004

(65) Prior Publication Data

US 2004/0245481 A1 Dec. 9, 2004

Related U.S. Application Data

(63) Continuation-in-part of application No. 10/021,827, filed on Dec. 13, 2001, now Pat. No. 6,702,984.

(60) Provisional application No. 60/255,308, filed on Dec. 13, 2000.

(51) Int. Cl.
H01J 33/00 (2006.01)

(52) U.S. Cl. .................................. 250/492.3
(58) Field of Classification Search ................ 250/306, 250/311, 455.11, 453.11, 454.11, 492.3
See application file for complete search history.

(56) References Cited

U.S. PATENT DOCUMENTS

| | | | |
|---|---|---|---|
| 2,913,619 A * | 11/1959 | Geisler, Jr. ............ 250/396 R |
| 3,582,650 A * | 6/1971 | Avery ........................ 250/399 |
| 3,780,308 A | 12/1973 | Nablo | |
| 4,074,313 A * | 2/1978 | Reisner et al. ........... 369/44.39 |
| 4,547,119 A * | 10/1985 | Chance et al. ............. 414/735 |
| 4,599,030 A * | 7/1986 | Skaalen et al. ............ 414/460 |
| 4,652,763 A | 3/1987 | Nablo | |
| 4,684,088 A * | 8/1987 | Heller ..................... 248/123.2 |
| 4,726,046 A * | 2/1988 | Nunan ......................... 378/65 |
| 4,760,567 A * | 7/1988 | Crewe ....................... 369/101 |
| 5,136,212 A | 8/1992 | Eguchi et al. | |
| 5,155,423 A * | 10/1992 | Karlen et al. .......... 318/568.11 |
| 5,229,607 A * | 7/1993 | Matsui et al. ............... 250/306 |
| 5,321,271 A * | 6/1994 | Schonberg et al. ...... 250/492.3 |
| 5,378,898 A | 1/1995 | Schonberg et al. | |
| 5,457,269 A | 10/1995 | Schonberg | |
| 5,530,255 A | 6/1996 | Lyons et al. | |
| 5,539,212 A | 7/1996 | Matthews et al. | |
| 5,561,298 A | 10/1996 | Cirlin et al. | |
| 5,603,853 A | 2/1997 | Mombo-Caristan | |
| 5,709,842 A | 1/1998 | Held et al. | |
| 5,744,811 A | 4/1998 | Schonberg et al. | |
| 5,882,487 A * | 3/1999 | Li et al. ................ 204/157.41 |
| 5,962,995 A | 10/1999 | Avnery | |
| 5,998,691 A | 12/1999 | Abel et al. | |
| 6,054,714 A | 4/2000 | Izutsu et al. | |

(Continued)

FOREIGN PATENT DOCUMENTS

JP 11-137645 5/1999

Primary Examiner—Jack I. Berman
(74) Attorney, Agent, or Firm—Hamilton, Brook, Smith & Reynolds, P.C.

(57) ABSTRACT

An apparatus for irradiating surfaces includes an electron beam generator for generating a beam of electrons. The beam of electrons exits the electron beam generator through an exit window. A robotic device moves the beam of electrons over the surfaces to irradiate selected regions of the surfaces. The robotic device includes a propulsion system for propelling the robotic device.

21 Claims, 17 Drawing Sheets

U.S. PATENT DOCUMENTS

| | | |
|---|---|---|
| 6,113,851 A | 9/2000 | Soloshenko et al. |
| 6,140,657 A | 10/2000 | Wakalopulos et al. |
| 6,188,075 B1 * | 2/2001 | Takayama et al. ....... 250/492.3 |
| 6,203,755 B1 | 3/2001 | Odland |
| 6,264,836 B1 | 7/2001 | Lantis |
| 6,702,984 B2 * | 3/2004 | Avnery ........................ 422/22 |
| 6,826,254 B2 * | 11/2004 | Mihara et al. ................ 378/64 |

* cited by examiner

IRRADIATION APPARATUS

RELATED APPLICATIONS

This application is a continuation-in-part of U.S. application Ser. No. 10/021,827, filed Dec. 13, 2001 now U.S. Pat. No. 6,702,984, which claims the benefit of U.S. Provisional Application No. 60/255,308, filed on Dec. 13, 2000. The entire teachings of the above applications are incorporated herein by reference.

BACKGROUND

Personnel working within environments contaminated with hazardous chemical or biological agents typically wear protective suits to prevent direct exposure to the hazardous agents. Since the outer surfaces of the suit can become covered with the hazardous agents during use, the user is in danger of becoming contaminated when the time comes to remove the suit. Therefore, it is apparent that there are instances where the skin and inner clothing of such personnel can come into contact with the hazardous agents. In addition, there may be situations where people not wearing protective clothing find themselves in a contaminated environment and become contaminated with such hazardous agents. Furthermore, rooms and objects such as vehicles, structures, furniture, equipment, etc., can become contaminated.

SUMMARY

The present invention is directed to an apparatus and method for irradiating surfaces which is suitable for decontaminating surfaces, including clothing or the skin on a person, or other living creatures, as well as irradiating and treating rooms and objects such as vehicles, structures, furniture, equipment, etc. The apparatus includes an electron beam generator for generating a beam of electrons. The beam of electrons exits the electron beam generator through an exit window. A robotic device moves the beam of electrons over the surfaces to irradiate selected regions of the surfaces. A propulsion system is included for propelling the robotic device.

In preferred embodiments, the propulsion system includes a first pair of rotatable wheels rotatably fixed and spaced apart from each other along a first axis. The first pair of wheels are rotatably driven. A second pair of rotatable wheels are spaced apart from each other along a second axis transverse to the first axis. The wheels of the second pair are also rotatably driven and each is pivotably mounted and steerable. Each wheel in the first and second pairs of rotatable wheels can be independently driven. In another embodiment, the robotic device can be moved along a track in a fixed path. The robotic device also includes a robotic arm for maneuvering the electron beam generator. The robotic device has a horizontal rotary joint for swinging the robotic arm. The robotic arm includes an upper arm member with a rotary shoulder joint rotatably coupled to the upper arm member for raising and lowering the robotic arm. A lower arm member is rotatably coupled to the upper arm member by a rotary elbow joint. The elbow joint raises and lowers the lower arm member relative to the upper arm member. A bracket is rotatably coupled to the lower arm member by a rotary wrist joint. The wrist joint swings the bracket from side to side. A rotary bracket joint rotatably couples the electron beam generator to the bracket for rotating the electron beam generator. The robotic device is capable of controllably spacing the exit window of the electron beam generator a desired distance away from the surfaces as the electron beam generator is moved over the surfaces. Such spacing can be performed actively and continuously. The electron beam generator is typically hermetically sealed and irradiation of the surfaces can be for purposes including any one of sterilization, decontamination, curing, destroying molecules and facilitating chemical reactions.

By having a propulsion system and a robotic arm, embodiments of the present invention are able to sufficiently maneuver the electron beam generator to irradiate the floor, walls and ceilings of a room. In addition, embodiments of the present invention can maneuver the electron beam generator around objects such as vehicles, structures, furniture, equipment, etc., for irradiating outer surfaces thereof. Such irradiation capabilities can be useful for decontaminating hazardous biological and chemical agents on surfaces of a room or object, as well as curing coatings, paints or inks on such surfaces.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

Figure 1:
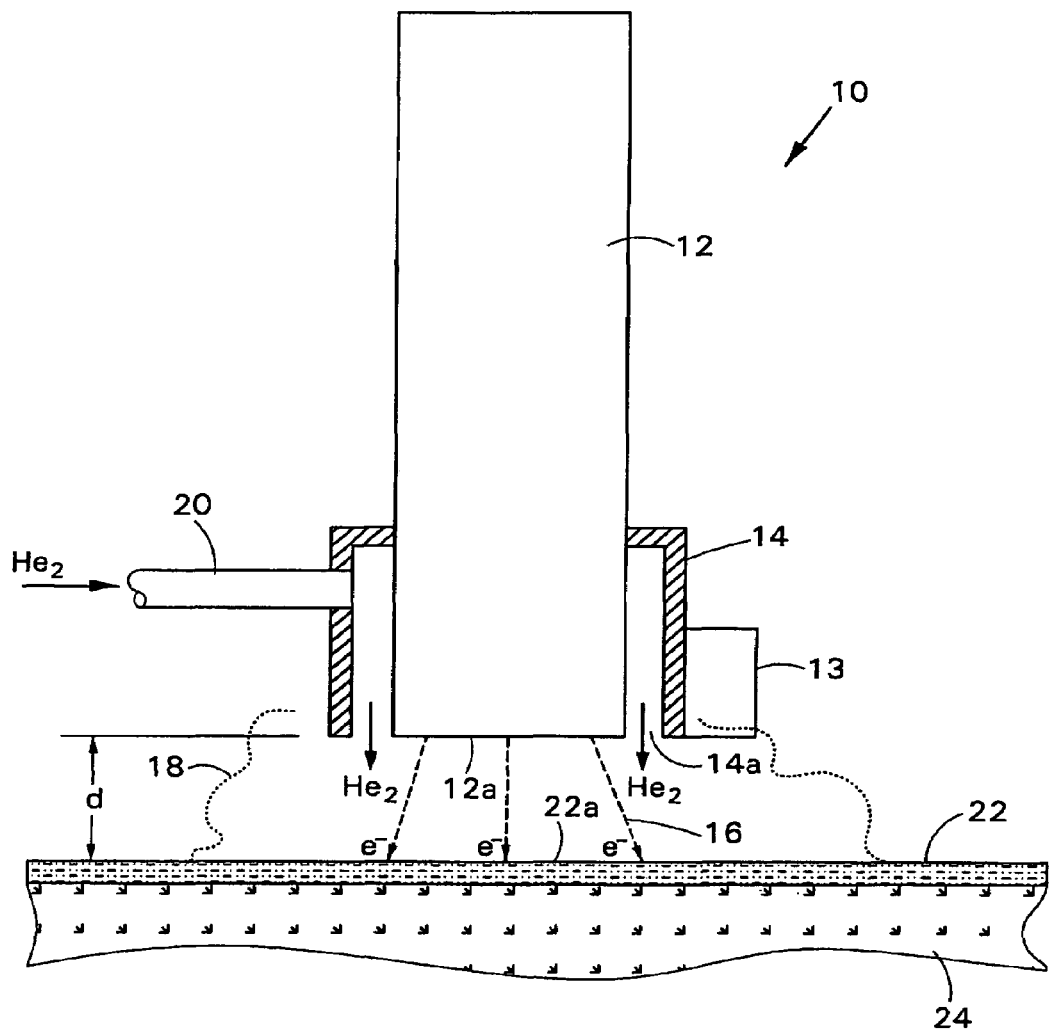
FIG. 1 is a schematic drawing of the present invention decontamination apparatus irradiating a section of skin, with the nozzle assembly shown in section.

Referring to FIG. 1, electron beam irradiation or decontamination apparatus 10 is employed for decontaminating surfaces having hazardous agents thereon and is suitable for decontaminating the clothes and skin of humans, as well as other living creatures. Decontamination apparatus 10 includes an electron beam generator 12 for producing a low power beam 16 of electrons e⁻ which exit the electron beam generator 12 through an exit window 12a. A nozzle assembly 14 is mounted to electron beam generator 12 and concentrically surrounds the exit window 12a. Nozzle assembly 14 is provided with an inert low density gas such as helium ($He_2$) from a supply line 20. Nozzle assembly 14 directs a curtain of the gas from outlet 14a which flows in substantially the same direction as the beam 16 of electrons e⁻. This produces a volume of low density gas 18 adjacent to and in front of the exit window 12a. Depending upon the flow rate of the gas and the proximity of electron beam generator 12 to the surface 22a to be irradiated, the volume of gas 18 may extend from the exit window 12a to the surface 22a as shown, to occupy the space therebetween. The volume of low density gas 18 increases the range of the beam 16 of electrons e⁻ and allows the beam 16 of electrons e⁻ to travel about seven times further than the distance obtainable when traveling through higher density air. Consequently, electron beam generator 12 can be of a low power, about 60 kV or less, with the electrons e⁻ capable of reaching the surface 22a to be irradiated from distances that ordinarily would be too far away.

Often, the surface 22a is a person's skin requiring decontamination from hazardous agents such as chemicals or biological agents (bacteria, viruses, etc.). The beam 16 of electrons e⁻ attacks the hazardous agents and renders them harmless. In the case of hazardous chemicals, the electron beam 16 converts the hazardous chemicals into harmless substances by causing chemical reactions. In the case of biological agents such as organisms, bacteria or viruses, the electron beam 16 kills the organisms, bacteria or viruses by disabling or destroying cellular structures. Since the electron beam 16 has low power of 60 kV or less, the electrons e⁻ penetrate and treat only the outer layer of dead skin 22 which is about 10 to 40 mm thick. Most x-rays generated are of low power and are also stopped at the outer layer of dead skin 22. The electrons e⁻ generated by an electron beam generator 12 operating at 60 kV or less have enough energy to decontaminate surface 22a but do not have enough energy to penetrate into the living epidermis 24, so that the living tissue experiences little or no damage. In addition, at such low power, the generation of x-rays is kept to a minimum.

When used for decontaminating living creatures such as people, electron beam generator 12 is preferably operated at 60 kV or less (usually 50 kV or less), with 40 kV to 50 kV being the typical range. At such voltages, typically the exit window 12a of electron beam generator 12 is positioned a distance "d" of about ¼ to ½ inches away from surface 22a with distances "d" of up to about 1 inches sometimes being possible, but more commonly possible when electron beam generator 12 is operated at about 60 kV. If the volume of gas 18 was not employed, the exit window 12a of electron beam generator 12 would normally have to be a maximum of about ⅛ inch away from surface 22a in order for the beam 16 of electrons e⁻ to pass through the air to reach surface 22a with sufficient energy for decontamination. A distance "d" of ⅛ inch is sometimes not practical for use on living creatures. The reason for this is that some living creatures have some surfaces that include curved and complex structures. Some of these structures have configurations with protrusions or recessed areas which prevent the electron beam generator 12 from being within ⅛ inches away from portions of the surfaces to be irradiated. Examples of such structures are the ears, nose, between the toes, etc., of some creatures. By having the increased range for the low power beam 16 of electrons e⁻, such difficult areas can be irradiated sufficiently for decontamination with little or no tissue damage. In other typical applications, decontamination apparatus 10 can be used to decontaminate the clothing of a person or the outer surfaces of a protective suit while worn by the user. When decontaminating clothes on a person, the clothes sometimes have wrinkles and folds in the material which form recesses or crevasses. The increased range of the low power beam 16 of electrons e⁻ allow such crevasses to be sufficiently irradiated for decontamination.

The inert low density gas 18 in front of the exit window 12a also provides inerting in the region of the beam 16 of electrons e⁻ to reduce or eliminate the formation of ozone ($O_3$). Ozone is typically formed by the interaction of the beam 16 of electrons e⁻ with oxygen ($O_2$) in the air and can be harmful if inhaled. Replacing the air in front of the exit window 12a with the inert gas 18 removes oxygen from the region which would have formed ozone.

Typically, electron beam generator 12 is a compact, hermetically sealed unit and can be similar to those disclosed in U.S. Pat. No. 5,962,995, U.S. patent application Ser. No. 09/349,592, filed Jul. 9, 1999, and U.S. patent application Ser. No. 09/209,024, filed Dec. 10, 1998, the contents of which are incorporated herein by reference in their entirety. Electron beam generator 12 is commonly in the range of about two inches in diameter and six to eight inches long for units operating in the range 40 kV to 60 kV. Alternatively, other suitable electron beam generators can be employed. Although nozzle assembly 14 is shown in FIG. 1 to surround the exit window 12a of electron beam generator 12, alternatively, the nozzle assembly 14 can be positioned adjacent to the electron beam generator 12. In addition, nozzle assembly 14 does not have to direct the low density gas 18 in the same direction as the electron beam 16 but instead can direct the gas 18 perpendicularly or at an angle to the electron beam 66.

Figure 2:
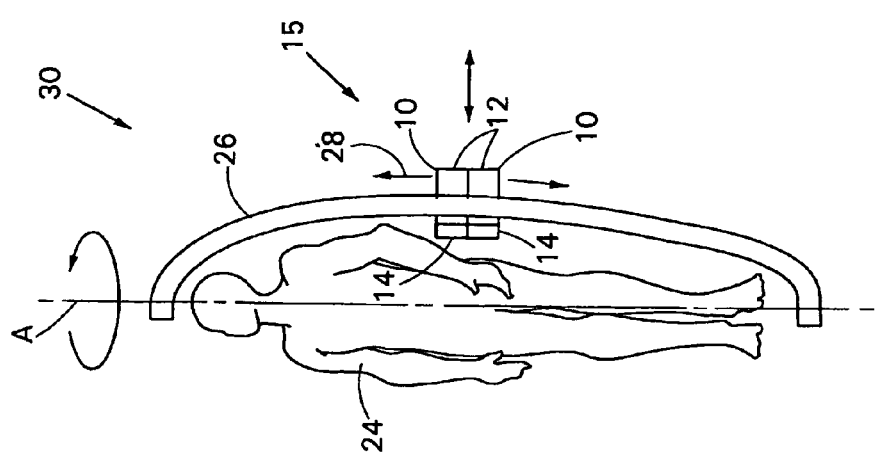
FIG. 2 is a schematic drawing of an embodiment of the present invention for irradiating a person's body.

In order to irradiate the entire body 24 of a person, decontamination apparatus 10 can be part of a decontamination apparatus 30 where the decontamination apparatus 10 forms an electron beam generator irradiation unit 15 that is mounted on a robotic arm 26, as shown in FIG. 2. The robotic arm 26 moves decontamination apparatus 10 around the body 24 for providing complete irradiation coverage. Additionally, more than one decontamination apparatus 10 can be mounted to robotic arm 26, as shown, to form the electron beam generator irradiation unit 15 in order to provide a larger irradiation region for obtaining a faster decontamination time. The robotic arm 26 may rotate around the body 24 about an axis A while vertically translating the irradiation unit 15 on a track up and down as shown by arrows 28. Typically, irradiation unit 15 is incrementally translated in the vertical direction after each rotation of robotic arm 26 around body 24 until the entire body 24 is irradiated. The irradiation unit 15 can also be translated laterally inwardly and outwardly relative to the body 24 to maintain the desired distance "d" between the exit windows 12a of the electron beam generators 12 and the surfaces of the body 24 in view that the surfaces of body 24 have variable distances from robotic arm 26. The irradiation unit 15 can be tilted in order to be properly orientated relative to the changing surfaces of body 24. In cases where there is more than one electron beam generator 12, the electron beam generators 12 can be independently translated laterally. The distance "d" can be continuously and actively controlled by a spacing device 13 (FIG. 1) mounted to each electron beam generator 12. In one embodiment, the spacing device 13 is a proximity sensor which controls the lateral translation of the associated decontamination apparatus 10. Although arm 26 is shown in FIG. 2 to rotate about axis A, alternatively, arm 26 may be stationary while vertically translating irradiation unit 15, in which case, the person stands on a rotary table that spins the body 24 about axis A.

Figure 3:
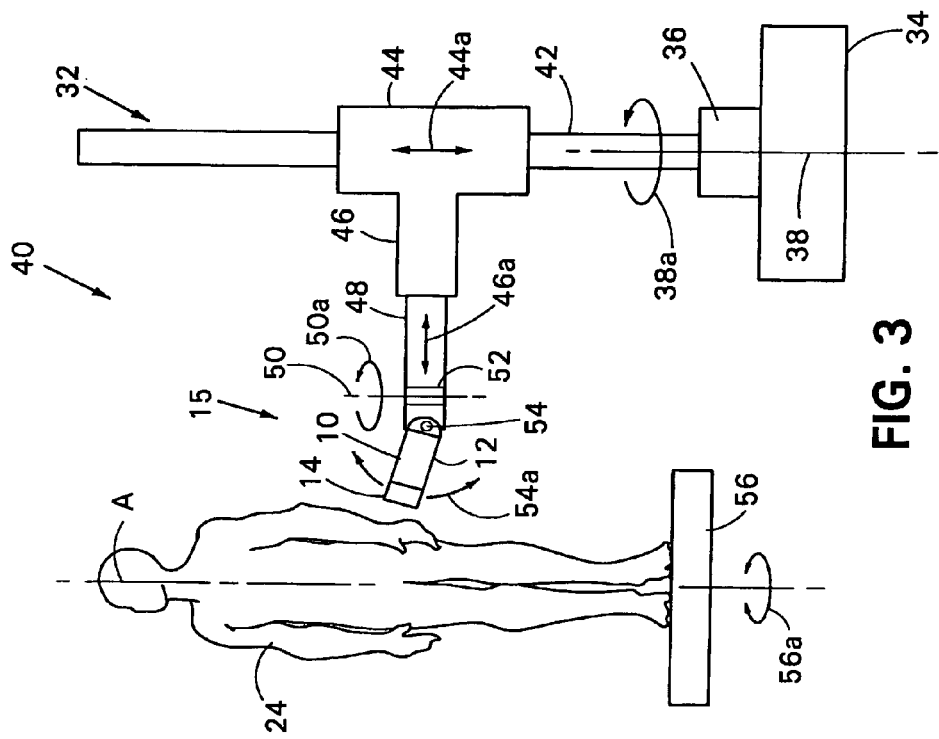
FIG. 3 is a schematic drawing of another embodiment of the present invention.

Referring to FIG. 3, decontamination apparatus 40 is another embodiment of the present invention in which the irradiation unit 15 is mounted to a conventional type robotic arm 32. As with decontamination apparatus 30, irradiation unit 15 can include one or more decontamination apparatuses 10. Robotic arm 32 includes a series of linear and rotating joints which allow the irradiation unit 15 to move over the surfaces of a person's body 24 for decontamination purposes. The robotic arm 32 shown in FIG. 3 includes a waist joint 36 rotatably mounted to a fixed base 34 about a vertical axis 38 for rotation in the direction of arrows 38a. A vertical post 42 extending along vertical axis 38 is mounted to waist joint 36. A shoulder joint 44 is mounted to post 42 for linearly translating vertically up and down the post 42 in the direction of arrows 44a. An arm 48 is mounted to the shoulder joint 44 for linearly translating laterally relative to shoulder joint 44 within portion 46 in the direction of arrows 46a. Arm 48 includes a first rotational joint 52 for rotation about axis 50 in the direction of arrows 50a and a second rotational joint 54 for rotation in the direction of arrows 54a about an axis that is perpendicular to axis 50. Irradiation unit 15 is distally mounted to arm 48 beyond joint 54. Waist joint 36 laterally pivots arm 48 and shoulder joint 44 raises and lowers arm 48 relative to body 24. Arm 48 translates irradiation unit 15 towards and away from body 24 within portion 46 of shoulder joint 44. Joints 52 and 54 pivot irradiation unit 15 relative to body 24.

As with decontamination apparatus 30, irradiation unit 15 is continuously and actively maintained at the desired distance "d" from the surfaces of body 24 by spacing device 13 while being maneuvered around body 24. If desired, the body 24 can stand on a rotary table 56 which rotates body 24 about axis A in the direction of arrows 56a. If a rotary table 56 is employed, the decontamination process can be accomplished more quickly. It is understood that the robotic arm 32 shown in FIG. 3 is an example of a robotic arm that can be employed, and that many other suitable variations or alternative robotic arms are possible. For example, joints can be added to or omitted from robotic arm 32. One such example is replacing shoulder joint 44 with a rotating joint that raises and lowers arm 48. Another example is combining joints 52 and 54 into a single joint. In addition, another linear joint for movement orthogonal to those depicted by arrows 46a and 44a can be added.

Figure 4:
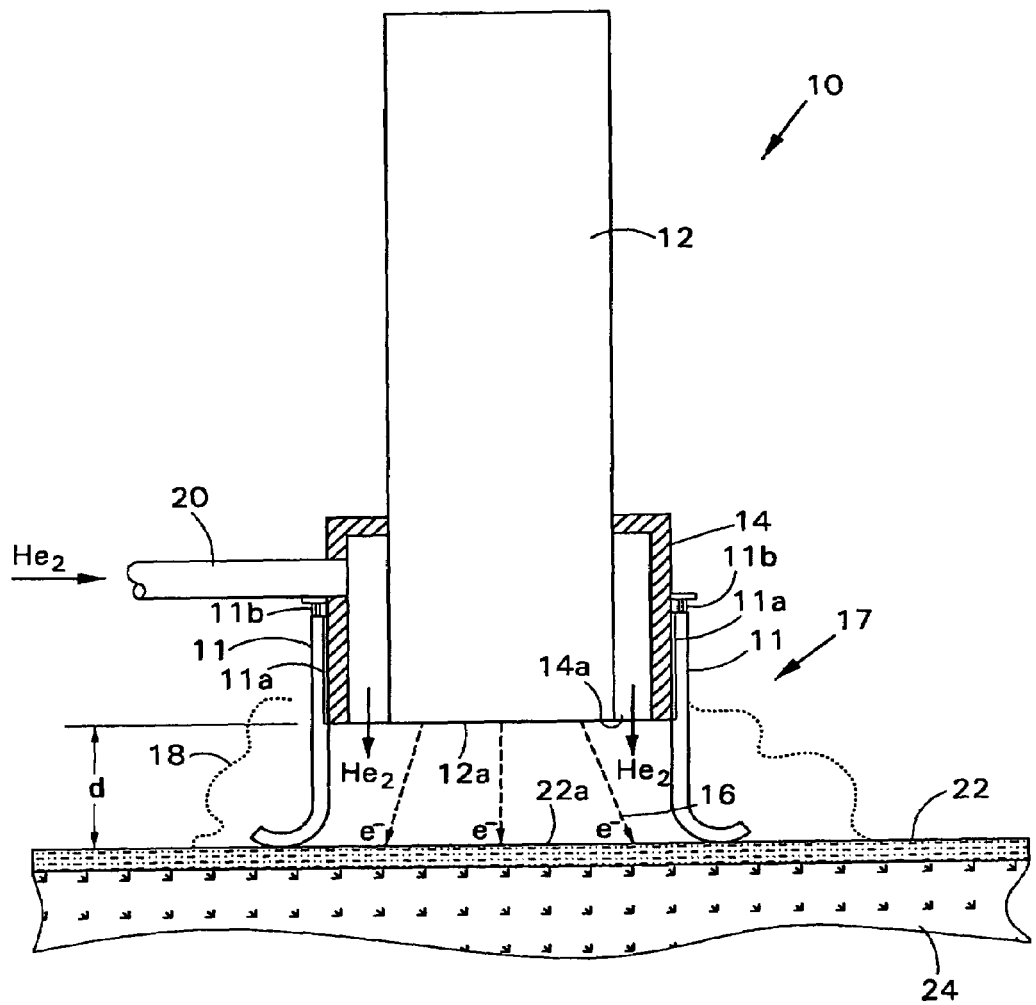
FIG. 4 is a schematic drawing of the present invention decontamination apparatus having a mechanical spacing device.

Referring to FIG. 4, decontamination apparatus 10 can include a mechanical spacing device 17 that includes one or more protrusions 11 mounted to the electron beam generator 12. Typically, the protrusions 11 are fixed to the nozzle assembly 14 and continuously and actively provide the proper distance "d" between the exit window 12a and the surface 22a by contacting the surface 22a. The distal ends of protrusions 11 can be curved as shown or can be straight. The mechanical spacing device 17 can be employed with a robotic arm 26/32 or can be employed when decontamination apparatus 10 is used as a hand held device. When mounted to a robotic arm 26/32, the mechanical spacing device 17 can also include pressure sensing elements 11a associated with the protrusions 11 for controlling the force at which the robotic arm presses the protrusions 11 against the surface 22a. In FIG. 4, the sensing elements 11a are shown to be fixed between protrusions 11 and nozzle assembly 14 to sense shear forces therebetween. Alternatively, protrusions 11 can press axially against a set of sensing elements 11b for sensing axial force. In addition, protrusions 11 can be spring load either vertically or pivotally for tripping a limit switch. Although multiple protrusions 11 have been shown in FIG. 4 to form spacing device 17, alternatively, spacing device 17 can also be formed by a single annular projection or hood. The hood may include slots or openings therethrough to allow the escape of gases.

When employed as a hand held device, decontamination apparatus 10 may include radiation shields for added protection and more than one decontamination apparatus 10 can be employed to form the irradiation unit 15. It is also understood if hand held, that decontamination apparatus 10 can employ either the mechanical spacing device 17 or the spacing device 13 depicted in FIG. 1, where the spacing device 13 is a proximity sensor. The proximity sensor can be connected to a distance indication system such as a speaker and/or an indicator light to provide an audible tone and/or a visible light when the proper distance "d" is obtained. The distance indication system can also include a distance meter or distance readout. The spacing devices 13/17 along with any associated equipment can be considered a spacing system.

Figure 6:
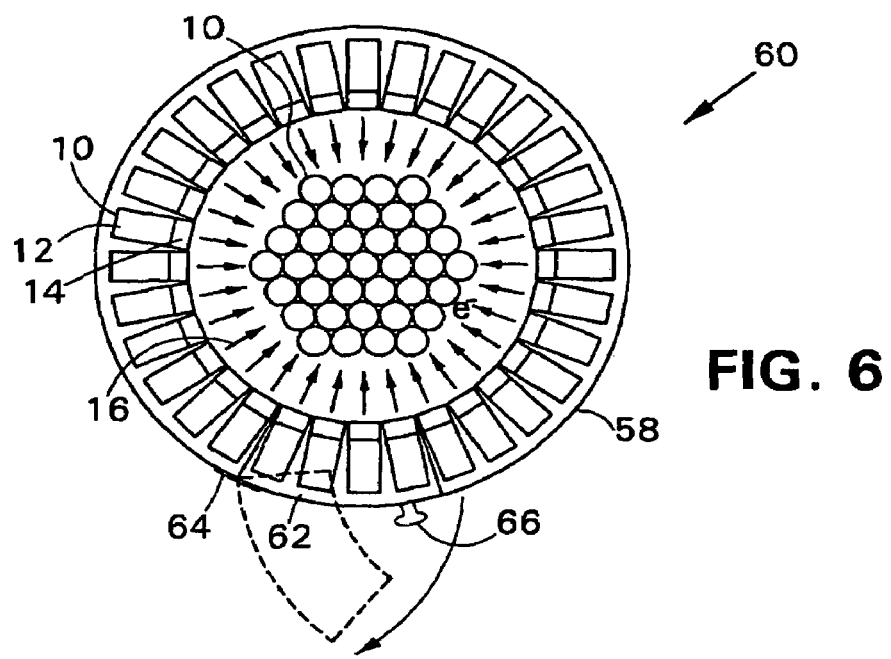
FIG. 6 is a plan schematic view of the embodiment depicted in FIG. 5 with the top removed.
Figure 5:
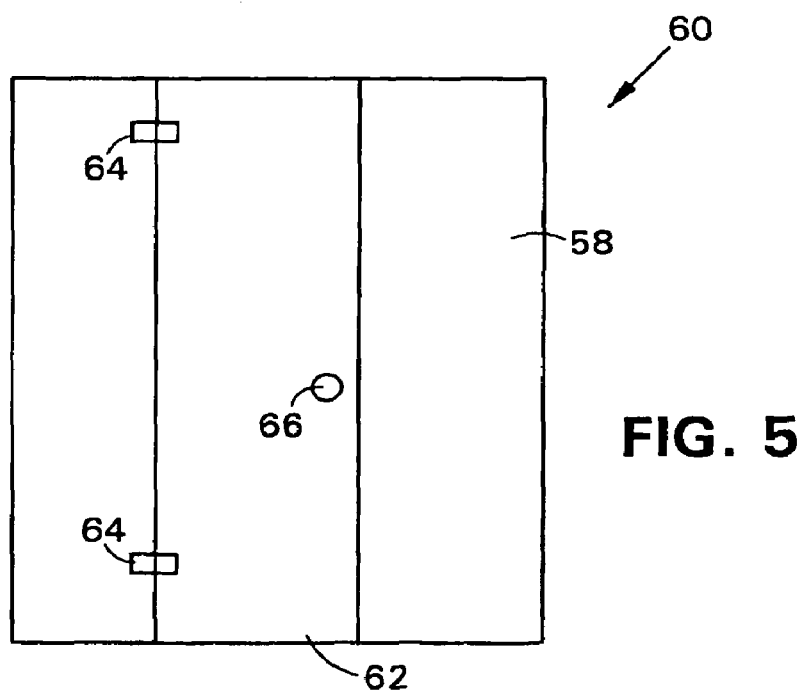
FIG. 5 is a front view of still another embodiment of the present invention.

Referring to FIGS. 5 and 6, decontamination apparatus 60 is still another embodiment of the present invention. Decontamination apparatus 60 includes an enclosure 58 containing a series of decontamination apparatuses 10 that are arranged to provide substantially uninterrupted electron beam coverage from the multiple surfaces of a body 24 standing within enclosure 58. Many of the surfaces of body 24 face on different directions. Some of the surfaces of body 24 are curved or angled relative to each other, or are on opposite sides of body 24, etc. A first lateral series of decontamination apparatuses 10 are arranged abutting each other and facing inwardly. This forms an enclosed lateral wall of electron beam generators 12 to generate a substantially continuous laterally directed wall or curtain of electron beams 16 inwardly into the enclosure 58 from substantially all sides or directions. In addition, a second vertical series of abutting decontamination apparatuses 10 are positioned at the bottom and the top of enclosure 58 for forming a floor and ceiling of electron beam generators 12 to generate a substantially continuous vertical shower of electron beams from axial ends of enclosure 58. Each decontamination apparatus 10 may be individually moveable inwardly and outwardly relative to the space within enclosure 58 for providing the proper distance "d" between the exit windows 12a of the electron beam generators 12 and the surfaces of a body 24. Spacing devices 13 or 17 can be employed for controlling the distance "d". Decontamination apparatus 60 is able to provide simultaneous irradiation of the surfaces of the entire body 24 from multiple directions, thereby providing fast or rapid decontamination.

In some cases, irradiation can be sequentially performed by decontamination apparatus 60 where only a portion of the electron beam generators 12 are irradiating at a given time. For example, the irradiation can be started at one part of the body 24, such as the head, and then the remaining electron beam generators 12 incrementally activated until the entire body 24 is irradiated. This may be helpful to prevent claustrophobia where only portions of the electron beam generators 12 are moved into position for irradiation at a given time. The electron beam generators 12 could be moved into position to irradiate as much as ¼ to ½ of the body 24 at the same time.

Entry into enclosure 58 is provide by a door 62 having a handle 66 and hinges 64. Alternatively, other suitable doors can be employed. For example, the longitudinal axis of enclosure 58 can be horizontal so that the door is at one axial end and the body 24 is inserted therein while lying horizontally. In such a design, a horizontal support may be provided for supporting the body 24 without blocking the electron beams 16. Although enclosure 58 is shown to be cylindrical in shape, alternatively, enclosure 58 may have a cross section that is rectangular, oval, polygonal, or combinations thereof. The enclosure 58 can also have an interior shape closely resembling a human shape. In addition, it is understood that the number of electron beam generators 12 employed is determined by the size of enclosure 58 and the size of the individual electron beam generators 12. Furthermore, decontamination apparatus 60 can be configured so that only a portion of body 24 is simultaneously irradiated, for example, half the body 24, which then is turned for irradiation of the other half. A rotary table 56 (FIG. 3) can be employed.

In the present invention, since the electron beam generators 12 can be made small in size, in some cases the electron beam generators 12 are able to maneuver close enough to the surfaces to be irradiated to provide sufficient decontamination without the use of the low density gas 18 and without damaging living tissue when irradiating skin. Although irradiation through air when an inert gas is not supplied results in the formation of ozone, if irradiation of a body 24 of a person can be performed within about 20 seconds, the person can hold his or her breath during the irradiation process to avoid inhalation of ozone. In other situations where the electron beam generators 12 are positioned closely to the surfaces to be irradiated (about ⅛ inches), a nozzle assembly 14 can be used to direct inert gases that are not necessarily low density for inerting purposes, such as nitrogen, argon, etc., to reduce or eliminate the formation of ozone.

Figure 7:
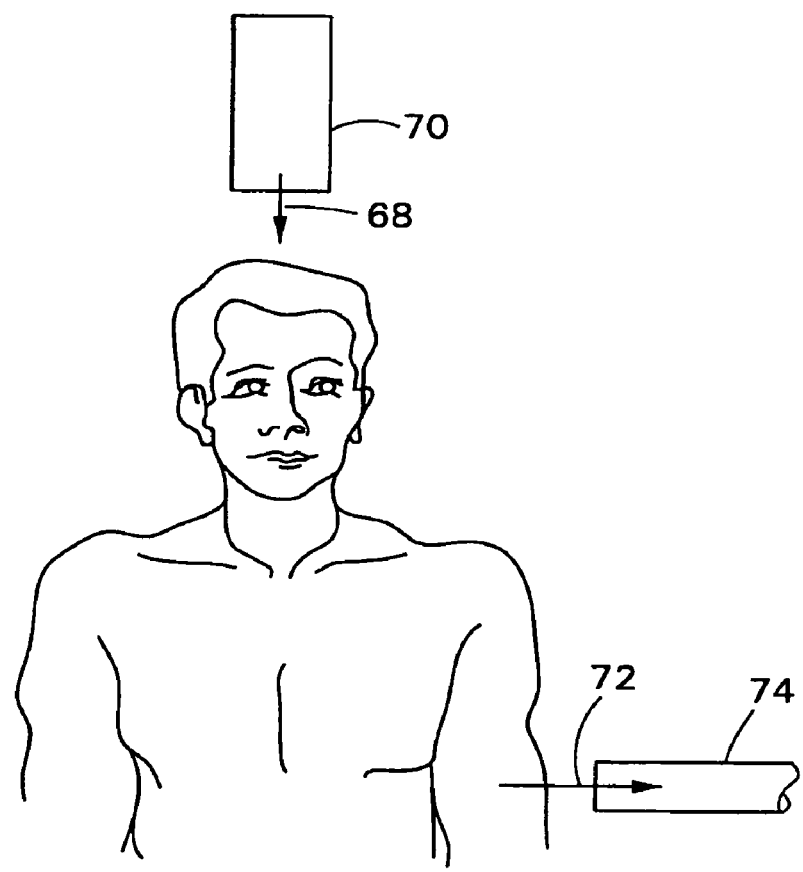
FIG. 7 is a schematic front view of an air/oxygen supply system providing a person with air or oxygen during irradiation, with gases undesirable for inhalation being removed by a gas removal system.

If the irradiation time takes longer than about 20 seconds, both when an inert gas is supplied or when irradiating through the air, the person can be provided with a supply of breathable air or oxygen 68 through an air/oxygen supply system 70, such as a nozzle assembly, from an air or oxygen supply as shown in FIG. 7. A gas removal or exhaust system 74, for example, a suction nozzle, can be provided for removing gases 72 undesirable for inhalation, such as the supplied inert gases and/or ozone. A blower system can also be employed as the gas removal system. The air/oxygen supply system 70 and the gas removal system 74 are either positioned to not interfere with the irradiation process or are movable. In some cases, the person may have to hold his/her breath initially until the head is decontaminated.

Figure 8:
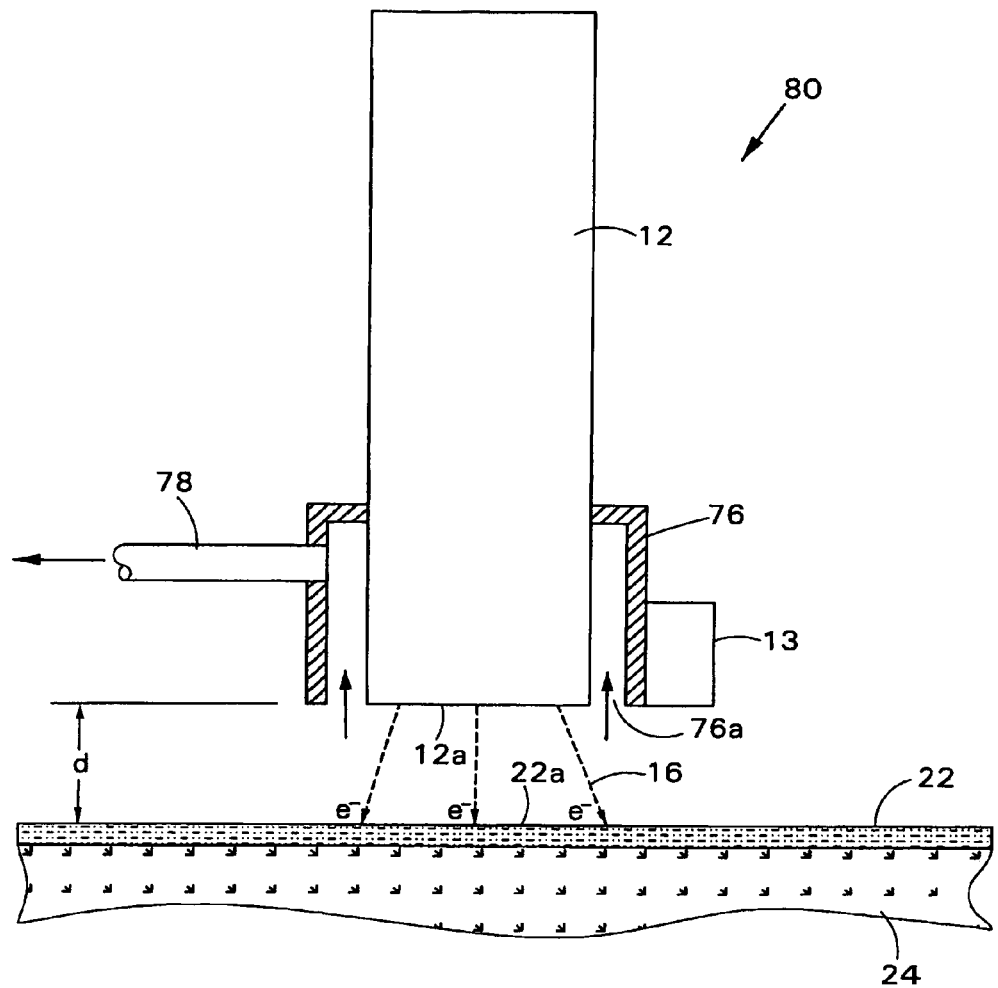
FIG. 8 is a schematic drawing of yet another embodiment of the present invention decontamination apparatus.

Referring to FIG. 8, electron beam irradiation or decontamination apparatus 80 is yet another embodiment of the present invention which differs from apparatus 10 depicted in FIG. 1 in that apparatus 80 includes a gas removal vacuum assembly 76 concentrically surrounding the exit window 12a of the electron beam generator 12 and mounted thereto. Gases including any generated ozone are drawn into the inlet 76a of vacuum assembly 76 from the region adjacent to exit window 12a, between surface 22a and exit window 12a, and then out vacuum line 78. This eliminates or reduces the amount of ozone in the region of apparatus 80. In some cases, the pressure in front of exit window 12a can be lowered, thereby increasing the range of the beam 16 of electrons e$^-$.

Figure 9:
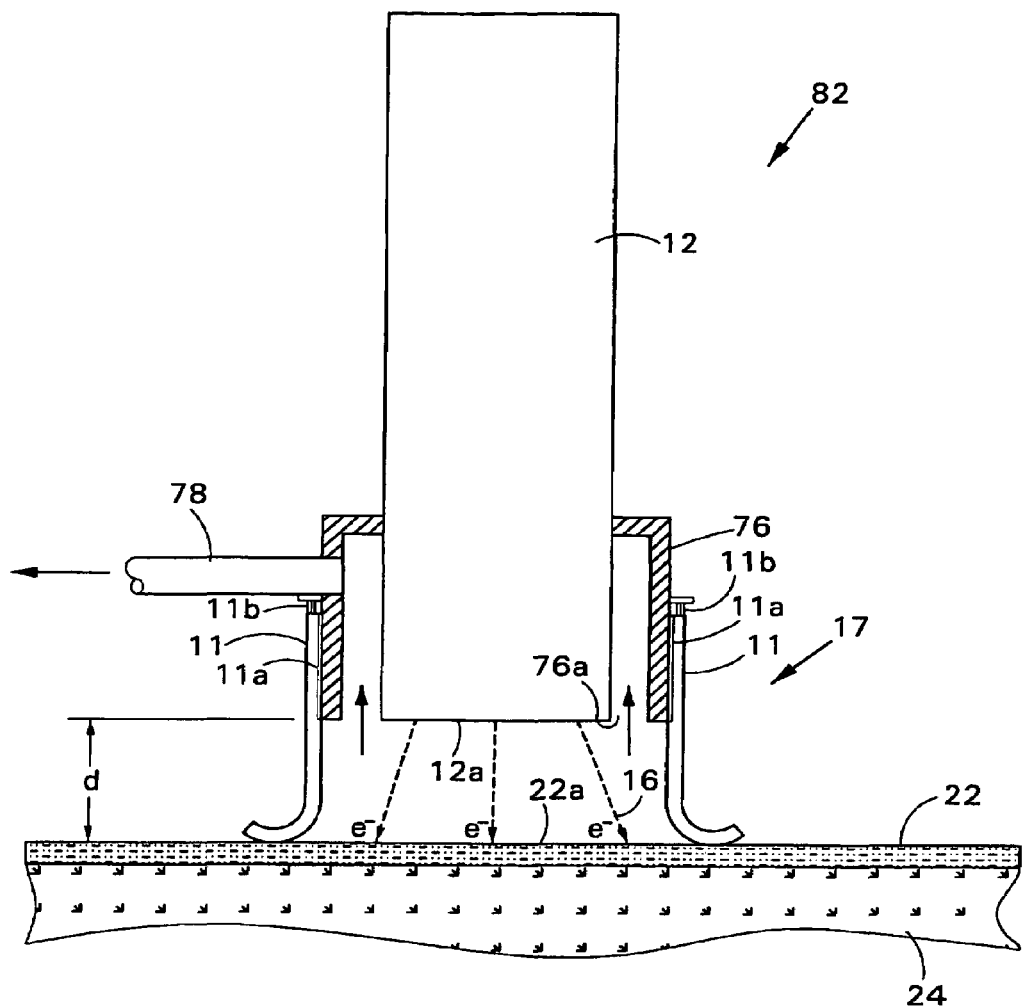
FIG. 9 is a schematic drawing of another embodiment of the present invention decontamination apparatus.

Referring to FIG. 9, electron beam irradiation or decontamination apparatus 82 is another embodiment of the present invention which differs from apparatus 10 depicted in FIG. 4 in that apparatus 82 includes the vacuum assembly 76 of FIG. 8. Typically, spacing device 17 is a hood or shroud with a single annular protrusion 11 which allows a greater decrease of the pressure in front of exit window 12a. This further increases the range of the beam 16 of electrons e$^-$, thereby increasing the distance "d" at which effective decontamination can be obtained. The protrusion 11 can be made with openings or slots therethrough to allow some flow of gases. Apparatuses 80 and 82 are typically employed without supplying inerting gases, but in some cases, providing inert gases can be desirable. The gas removal or exhaust arrangements described above as well as the supply of inerting gases can be among other things, referred to as ozone reduction systems.

Although the present invention decontamination apparatuses have been described for decontaminating clothing and living creatures, the decontamination apparatuses may be used for any suitable irradiation application. Such applications may include the irradiation of non-living objects, materials or substances for sterilization, curing, or facilitating chemical reactions. Furthermore, electron beam generators 12 having power higher than 60 kV or lower than 40 kV may be used. In cases where non-living objects, materials or substances are to be irradiated, electron beam generators 12 can operate well above 60 kV, for example, 125 kV or greater. The low density gas 18, when used, allows the electron beam generators 12 to be positioned farther away from the objects, materials or substances than normally possible without the low density gas. Such increased range of the beam 16 of electrons e$^-$ also permits deeper penetration into the objects, materials or substances as well as more thorough irradiation of complex geometries. There may be situations when irradiating non-living objects, materials or substances in which supplying other inert gases is desirable. Also, the removal of gases with a gas removal system may be desirable.

Figure 10:
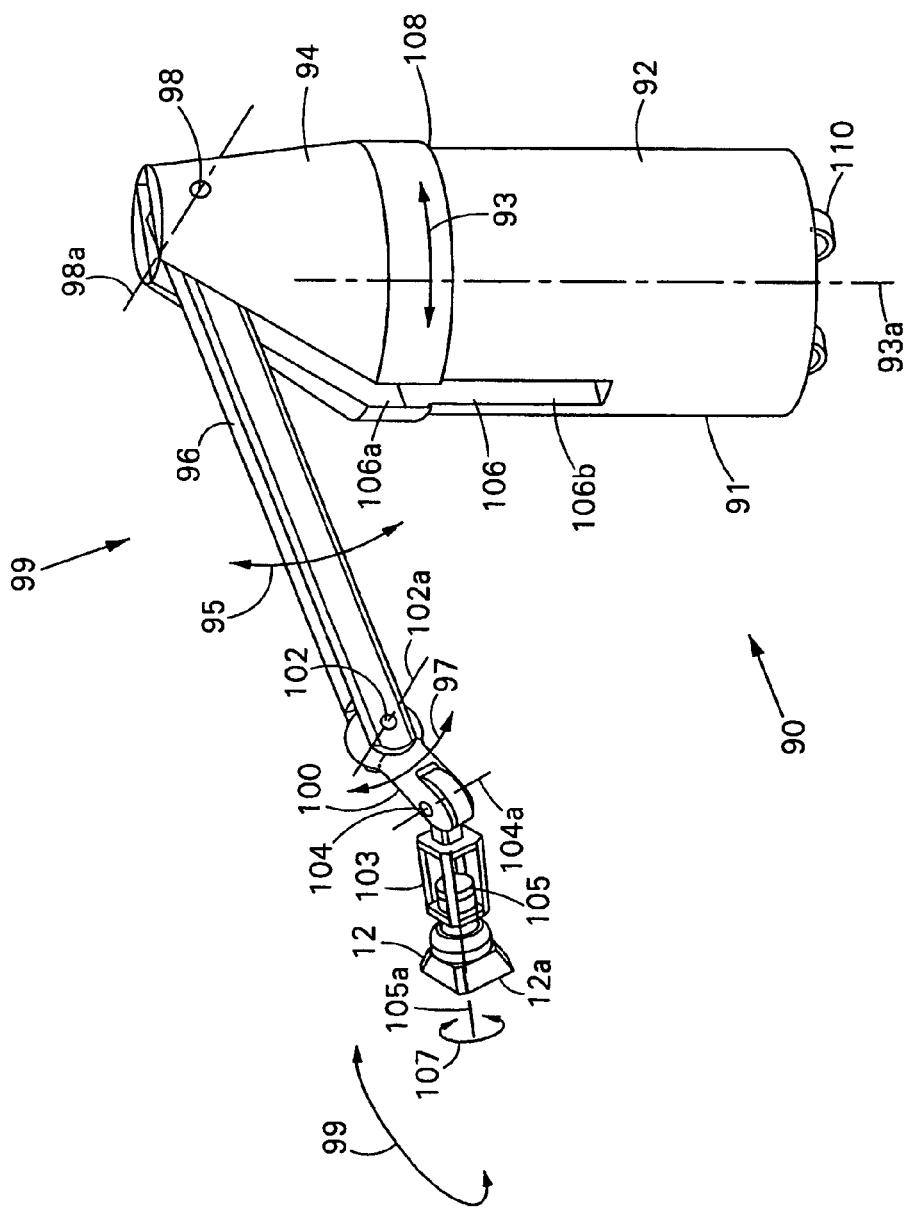
FIG. 10 is a perspective view of a mobile robotic irradiation apparatus in the present invention.
Figure 12:
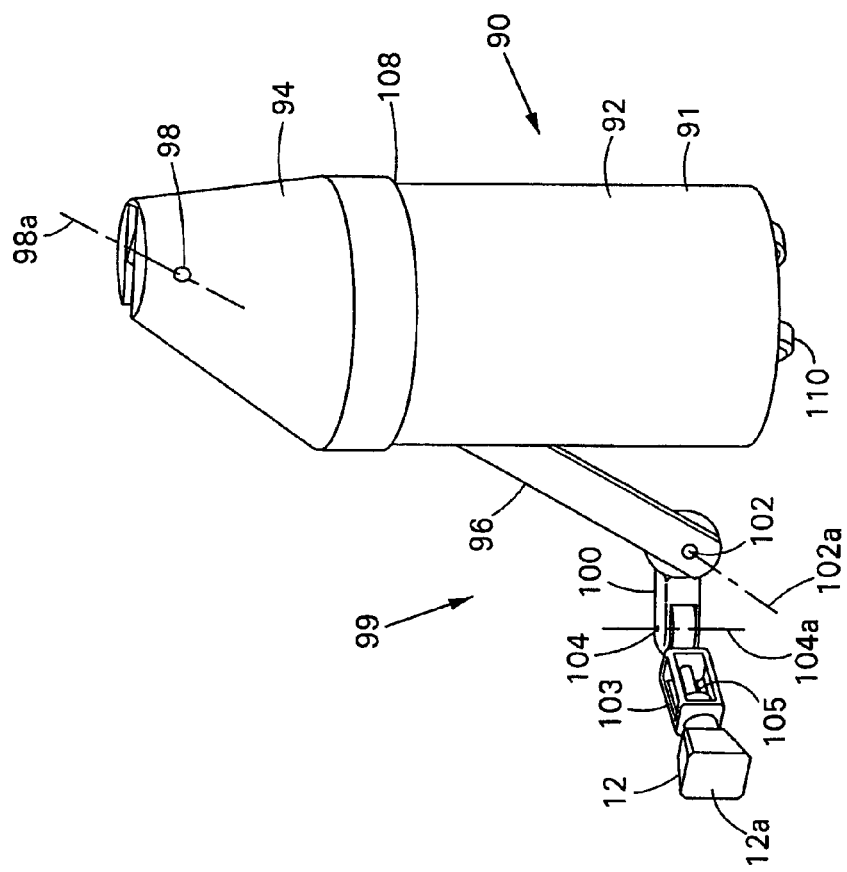
FIG. 12 is a perspective view of the mobile robotic irradiation apparatus positioned for irradiating lower vertical surfaces.

Referring to FIG. 10, mobile robotic irradiation apparatus 90 is another embodiment of the present invention. Apparatus 90 includes a mobile robot 91 having a maneuverable arm 99 for maneuvering an electron beam generator 12 mounted at the distal end for irradiating surfaces with a beam 16 of electrons e$^-$. Surfaces can be irradiated for purposes including sterilization, decontamination, curing, destroying molecules, facilitating chemical reactions, etc. Any of the spacing devices described earlier can be included for spacing the exit window 12a the proper distance from the surfaces to be irradiated and, depending upon the situation at hand, a gas supply system may or may not be employed. The exit window 12a can be made rectangular or square, as shown in FIG. 12, for allowing positioning within corners such as in a room. The housing of electron generator 12 in the region of the exit window 12a is shown to be flared outwardly in a rectangular or square manner. An exit window that is about 4 inches by 4 inches is typically suitable for most applications, although larger, smaller, or round exit windows 12a may be suitable in particular instances. When irradiating nonliving surfaces, a higher power beam 16 of electrons e⁻ can be generated than when irradiating living surfaces. Such higher power beams 16 of electrons e⁻ allow the exit window 12a of electron beam generator 12 to be spaced a distance "d" that is farther away than when employing the lower power beams 16 of electrons e⁻.

Figure 18:
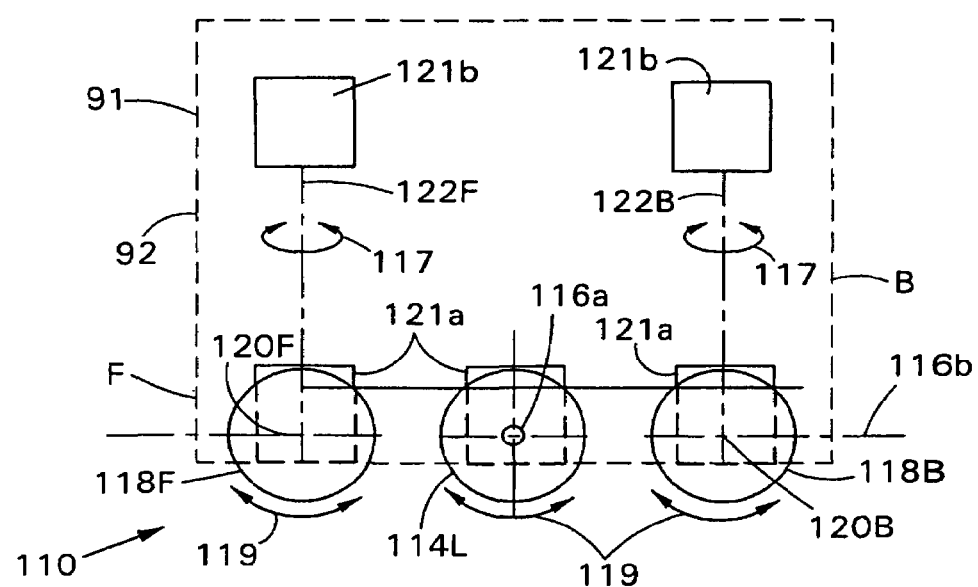
FIG. 18 is a side schematic view of the propulsion system of the mobile robotic irradiation apparatus.
Figure 19:
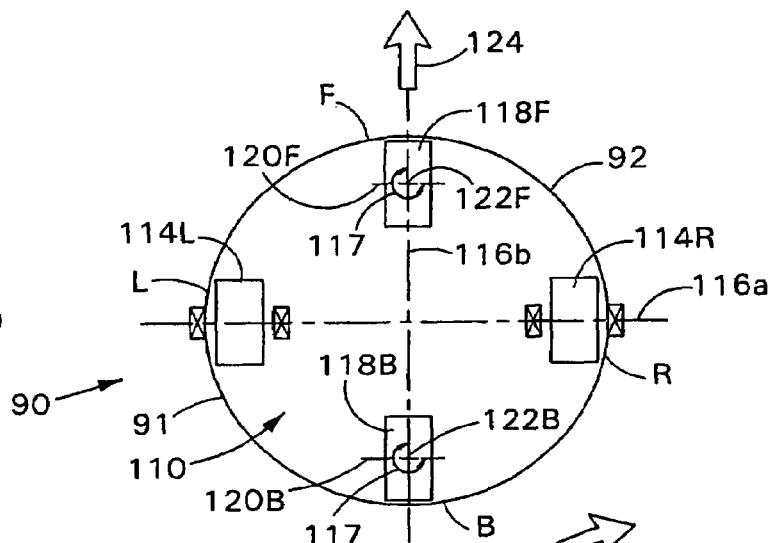
FIGS. 19–21 are plan schematic views of the propulsion system of the mobile robotic irradiation apparatus with the wheels positioned for providing various directions of motion.
Figure 20:
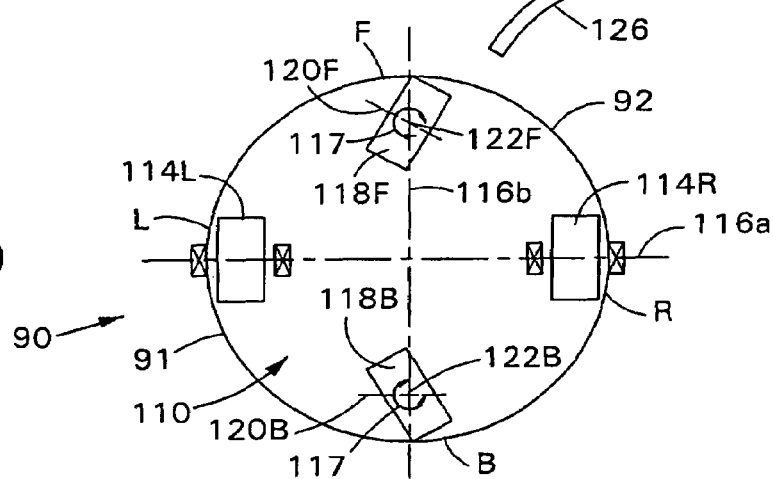

The mobile robot 91 includes base 92 having a propulsion system 110 for steerably propelling the robot 91 and irradiation apparatus 90. The propulsion system 110 typically includes a series of wheels 114L/114R and 118F/118B (FIGS. 18–20). A turret 94 is rotatably mounted to the base 92 by a rotary waist joint 108. The waist joint 108 provides 360° of horizontal rotary motion of the turret 94 about a vertical axis 93a in the direction of arrows 93 for swinging maneuverable arm 99 horizontally. The maneuverable arm 99 has an upper arm member 96 which is rotatably mounted to turret 94 by a rotary shoulder joint 98. The shoulder joint 98 provides about 180° of rotary motion of the upper arm member 96 and maneuverable arm 99 about a horizontal axis 98a in the direction of arrows 95 for raising and lowering the maneuverable arm 99. A slotted recess 106 having an upper portion 106a in the turret 94 and a lower portion 106b in the base 92 allow the upper arm member 96 to be lowered therein for increased range of motion, especially when angling arm member 96 downwardly. A lower arm member 100 is rotatably mounted to upper arm member 96 by a rotary elbow joint 102. The elbow joint 102 provides about 270° of rotary motion of the lower arm member 100 about a horizontal axis 102a in the direction of arrows 97 to raise and lower or swing arm member 100. A cage or bracket 103 which houses or supports electron beam generator 12 is rotatably mounted to the lower arm member 100 by a rotary wrist joint 104. The wrist joint 104 provides about 270° of side to side rotary swinging motion about axis 104a in the direction of arrows 99. The orientation of axis 104a changes with the position of shoulder joint 98 and elbow joint 102. The electron beam generator 12 is rotatably connected to cage or bracket 103 by a rotary cage or bracket joint 105. Rotary cage joint 105 provides 360° of rotary or spinning motion of electron beam generator 12 about axis 105a in the direction of arrows 107. This allows the exit window 12a of electron beam generator 12 to be appropriately positioned, such as in a corner. The propulsion system 110, waist joint 108, shoulder joint 98, elbow joint 102, wrist joint 104, and cage joint 105 are typically driven by drive motors (for example, drive motors 121a in propulsion system 110, FIG. 18), and allow the electron beam generator 12 to be moved or positioned for irradiating two-dimensional and three-dimensional surfaces. The drive motors for the robot 91 and propulsion system 110 are typically rotary servo or stepper motors which are connected to and controlled by a computer, usually housed in the base 92.

When the surfaces to be irradiated are larger than the size of the beam 16 of electrons e⁻, the electron beam generator 12 and beam 16 of electrons e⁻ are moved over the surfaces in a progressive overlapping manner to incrementally irradiate the surfaces. The movement of electron beam generator 12 and the beam 16 of electrons e⁻ can be preprogramed or can be continuously and actively determined in real time. The irradiation can be employed to cure coatings, paints and inks, kill bacteria and viruses, convert hazardous substances into non-hazardous materials, initiate or aid chemical reactions, etc.

Figure 11:
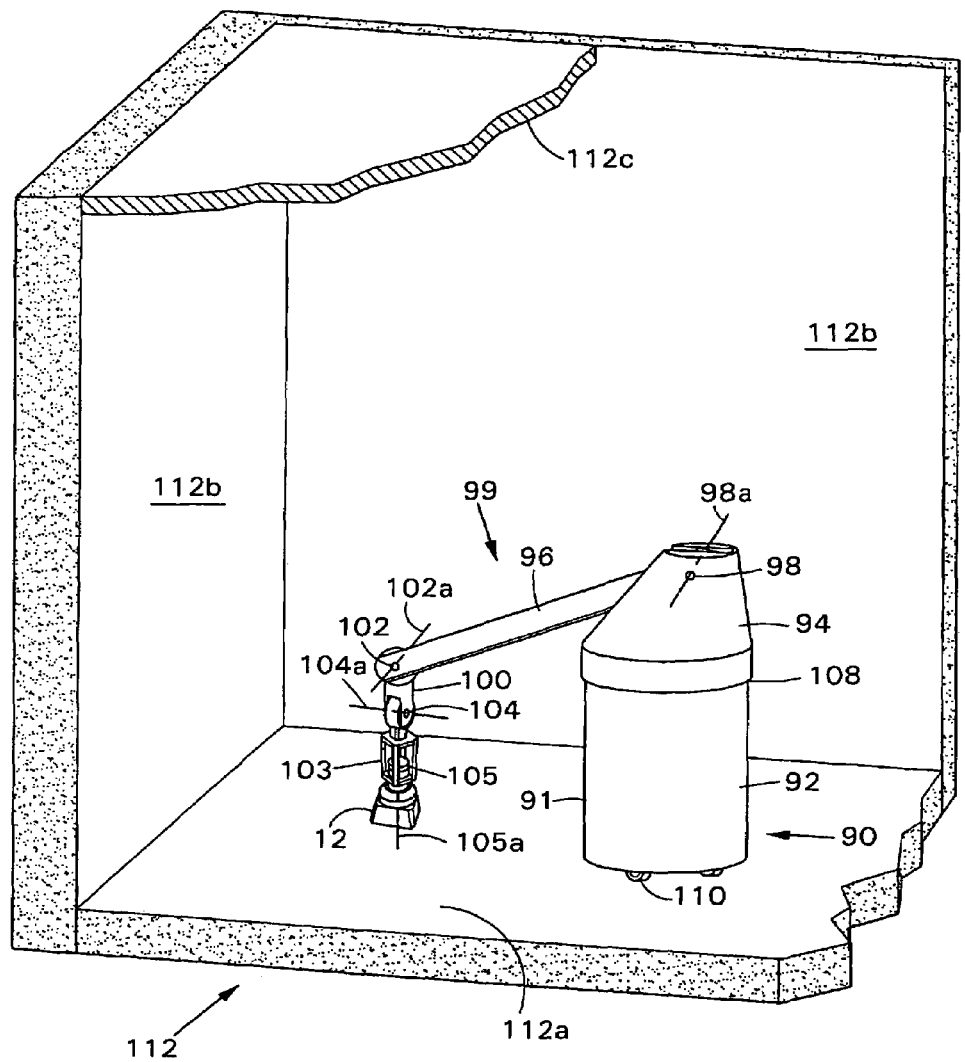
FIG. 11 is a perspective view of the mobile robotic irradiation apparatus positioned for irradiating floor surfaces in a room.

For example, referring to FIG. 11, irradiation apparatus 90 is shown positioned within a room 112 having a floor 112a, walls 112b and ceiling 112c with the maneuverable arm 99 pivoted about shoulder joint 98 to be angled downwardly. Maneuverable arm 99 is also bent at the elbow joint 102 to position the electron beam generator 12 in a vertical position in close proximity to the floor 112a. In such a position, the electron beam generator 12 is able to irradiate the surfaces of the floor 112a, for example, for sterilization or decontamination purposes. The electron beam generator 12 is also shown rotated about rotary joint 105 to orient exit window 12a for irradiating the corner of room 112. The electron beam generator 12 can be moved over the floor 112a by moving the robot 91 with propulsion system 110, by moving maneuverable arm 99, or a combination of the two. The distance "d" between exit window 12a and the surfaces to be irradiated can be continuously and actively controlled by a spacing device, when employed. By moving the electron beam generator 12 back and forth over the floor 112a in successive passes so that the coverage of the beam 16 of electrons e⁻ from each pass slightly overlaps each other, continuous irradiation coverage of the floor 112a or desired regions thereof by the beam 16 of electrons e⁻ can be obtained in increments. In some situations, irradiation of only a selected region or regions may be desired. If electron beam generator 12 is irradiating surfaces while robot 91 is propelled by propulsion system 110, maneuverable arm 99 may make slight movements to compensate for irregularities in the surface of floor 112a which can cause tilting of the robot 91 and/or vary the distance of the electron beam generator 12 from the floor 112a.

Figure 14:
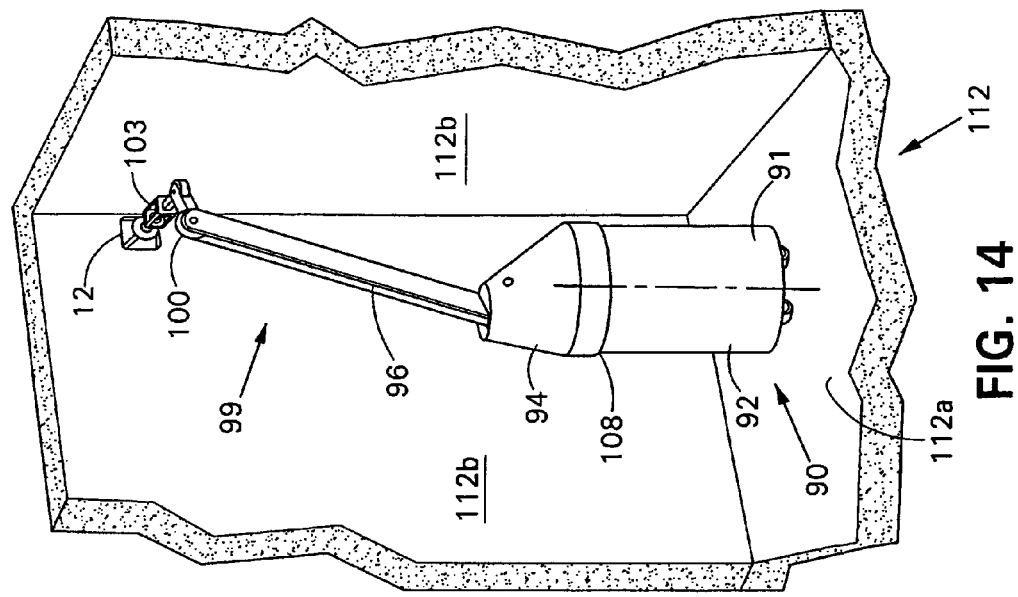
FIG. 14 is a perspective view of the mobile robotic irradiation apparatus within a room irradiating upper wall surfaces in a corner of the room.
Figure 13:
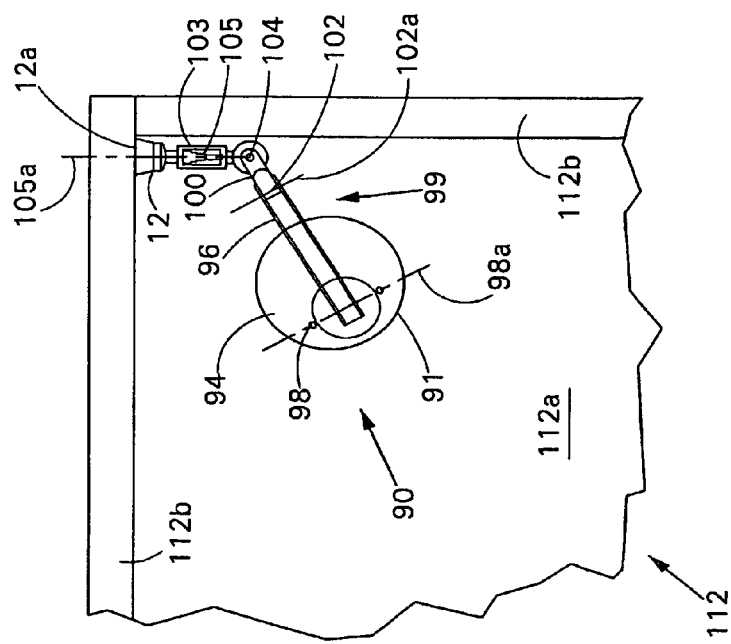
FIG. 13 is a plan view of the mobile robotic irradiation apparatus within a room irradiating wall surfaces in a corner of the room.
Figures 15, 16:
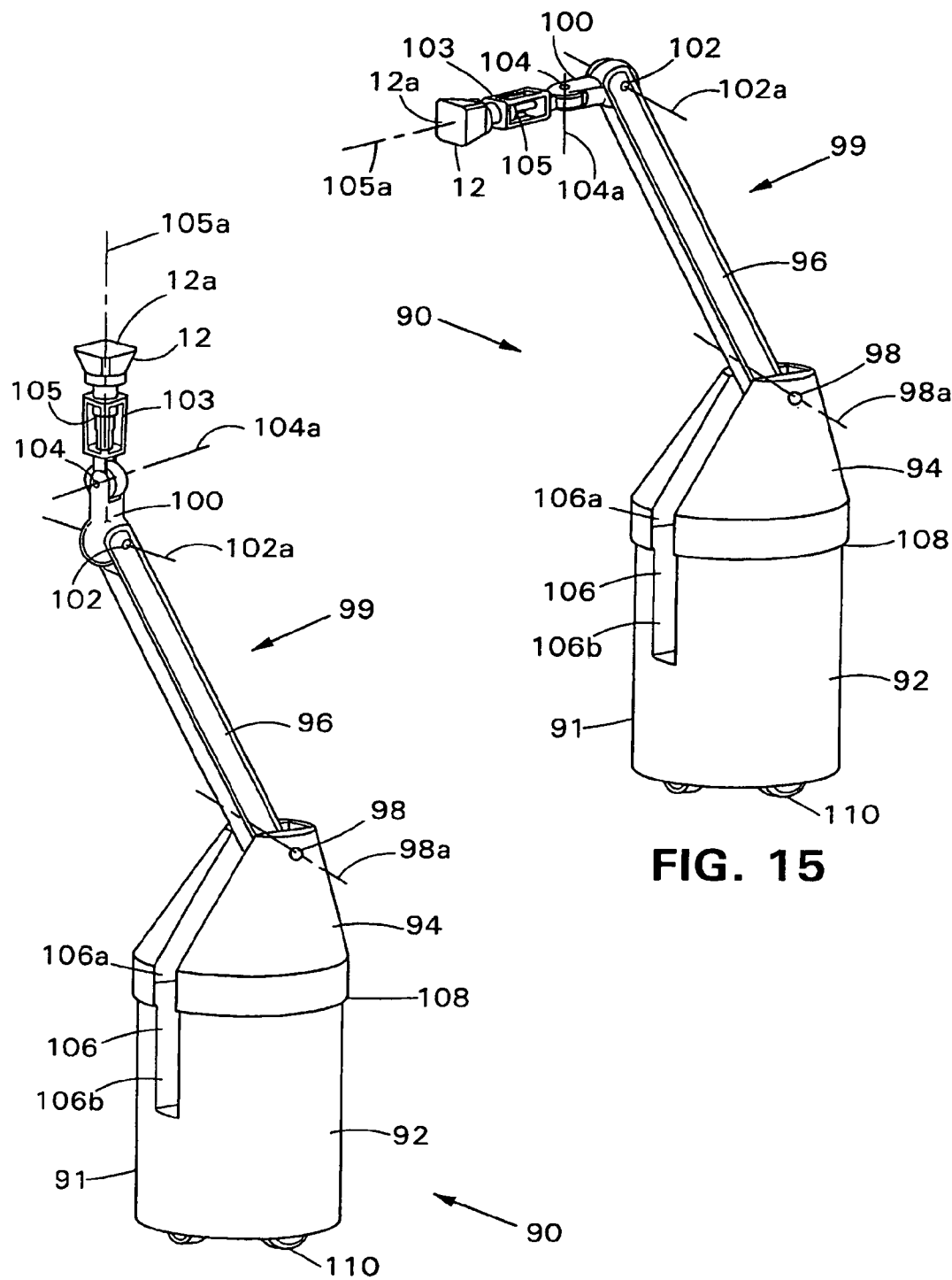
FIG. 15 is a perspective view of the mobile robotic irradiation apparatus positioned for irradiating elevated vertical surfaces.
FIG. 16 is a perspective view of the mobile robotic irradiation apparatus positioned for irradiating downwardly facing elevated surfaces.

Referring to FIG. 12, irradiation apparatus 90 is shown positioned for irradiating vertical surfaces such as surfaces of a wall 112b. When irradiating the lower portions of vertical surfaces, the maneuverable arm 99 can be pivoted downwardly at shoulder joint 98, bent at elbow joint 102 so that lower arm member 100 is positioned horizontally, and depending upon the position of robot 91 or the surface to be irradiated, the electron beam generator 12 can be pivoted about wrist joint 104 as shown. Referring to FIG. 13, pivoting the wrist joint 104 allows electron beam generator 12 to irradiate surfaces of a wall 112b in the corner where two walls 112b come together by positioning robot 91 away from the adjoining wall 112b. In addition, electron beam generator 12 is rotated about axis 105a to orient the exit window 12a in the proper orientation for positioning in the corner. When irradiating the corner between walls 112b, the irradiation apparatus 90 can be first positioned as shown in FIG. 12 to start at the bottom and then the upper arm member 96 is pivoted upwardly to irradiate the wall 112b in an upwardly moving direction. The elbow joint 102 can be pivoted simultaneously to maintain electron generator 12 in a straight vertical path. When in the upper position, the maneuverable arm 99 is pivoted upwardly about shoulder joint 98 with the elbow joint 102 being bent as shown in FIG. 14. If needed, waist joint 108 can be pivoted. In addition, the position of robot 91 can be adjusted by propulsion system 110 during irradiation. Alternatively, the direction of irradiation can be from top to bottom. When irradiating upper surfaces of wall 112*b* away from the corner, the wrist joint 104 does not need to be bent as shown in FIG. 15. The wall surfaces 112*b*, or desired regions thereof, are typically irradiated with vertical or horizontal movement of electron beam generator 12 or combinations thereof. In addition, slanted or arched movement can be employed.

FIG. 16 depicts irradiation apparatus 90 positioned for irradiating downwardly facing upper surfaces, such as a ceiling 112*c* (FIG. 11). Maneuverable arm 99 is pivoted in an upwardly angled or pointed manner about shoulder joint and elbow joint 102 can be bent to vertically orient electron beam generator 12, depending upon the ceiling height. The robot 91 is moved relative to ceiling 112*c* to irradiate the ceiling 112*c* or desired regions thereof with electron beam generator 12. Maneuverable arm 99 may also require movement, with joints 98, 102, 104, 105 and 108 pivoting when necessary.

Figure 17:
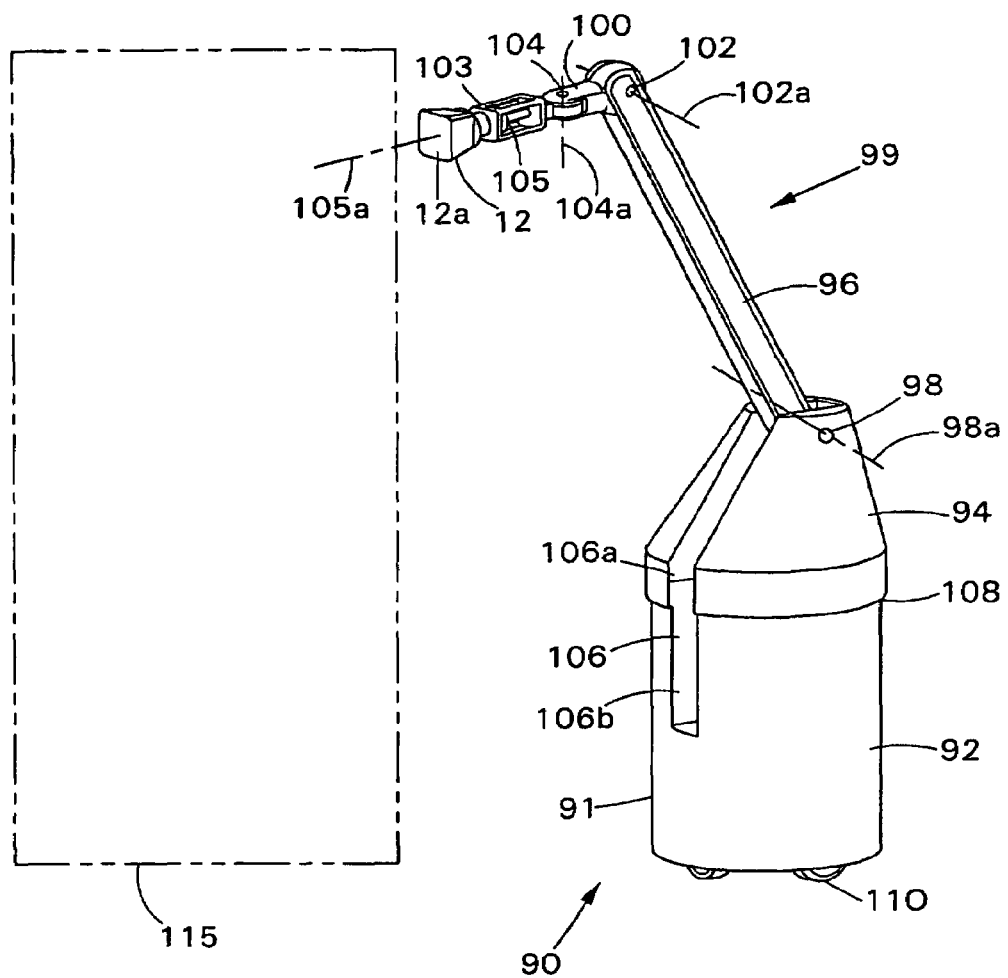
FIG. 17 is a perspective view of the mobile robotic irradiation apparatus irradiating an object.

Referring to FIG. 17, in addition to irradiating interior surfaces of a room 112, irradiation apparatus 90 can move electron beam generator 12 around an object 115 such as a vehicle, structure, furniture, equipment, etc., for irradiating exterior surfaces thereof with a beam 16 of electrons e⁻. The electron beam generator 12 is moved around object 115 or desired regions thereof by moving robot 91 around object 115 as well as manipulating maneuverable arm 91. This allows irradiation of large or irregularly shaped objects 115 that cannot fit within a self contained irradiation unit. Examples of such irradiation can be the sterilization/decontamination of object 115 or the curing of coatings thereon.

Referring to FIGS. 18–21, the propulsion system 110 of robot 91 in one embodiment includes a first pair of drive wheels having a right drive wheel 114R and a left drive wheel 114L which are rotatably mounted or fixed along a common horizontal axis 116*a* (FIG. 19) on opposite sides of base 92. Each drive wheel 114R/114L is independent from the other and can be driven in the direction of arrows 119 (FIG. 18) in unison or independently driven in both speed and direction. A second pair of steerable wheels having a front steerable drive wheel 118F and a back steerable drive wheel 118B are rotatably mounted along respective horizontal axes 120F and 120B on opposite sides of base 92 between wheels 114R/114L. Each steerable drive wheel 118F/118B is independent from the other and can be driven in the direction of arrows 119 (FIG. 18) in unison, or independently driven in both speed and direction relative to each other as well as drive wheels 114R/114L. Each steerable drive wheel 118F and 118B is also pivotably mounted along respective vertical axes 112F and 122B (FIG. 18) allowing each steerable drive wheel 118F/118B to be rotated or pivoted in the direction of arrows 117 to provide steering for robot 91. The steerable drive wheels 118F/1118B can be steered in the same direction in unison or independently steered in different directions (FIG. 20). In addition, the vertical axes 112F/122B are positioned along a common horizontal axis 116*b* which is positioned midway between wheels 114R/114L and is perpendicular to axis 116*a*. The drive wheels 114R, 114L, 120F and 120B are, in one embodiment, positioned equidistant from each other as shown. Each drive wheel 114R, 114L, 120F and 120B is coupled to and independently driven by a respective drive motor 121*a* for providing rotational motion in the direction of arrows 119. In addition, drive wheels 120F and 120B are independently coupled to and pivotably rotated or steered about axes 122F/122B in the direction of arrows 117 by respective drive motors 121*b*.

In use, referring to FIG. 19, in order to obtain movement in a straight forward direction as shown by arrow 124, the steerable drive wheels 118F and 118B of propulsion system 110 are first aligned in the same direction as drive wheels 114R/114L. The drive wheels 114R, 114L, 118F and 118B are then equally driven in unison in the same forward direction towards the front F of robot 91, resulting in the straight movement of robot 91 in the direction of arrow 124. Driving wheels 114R, 114L, 118F and 118B in the opposite direction towards the back B of robot 91 would produce movement of robot 91 in a straight backward direction.

Referring to FIG. 20, to obtain an arched turn in the right forward direction as shown by arrow 126, the front steerable drive wheel 118F is turned about axis 122F to the right and at an angle in the direction of the turn, and the back steerable drive wheel 118*b* is turned about axis 122B to the left or in the opposite direction, but at an angle of equal amount, as shown. The steerable drive wheels 118F/118B are each driven forward toward the front F of robot 91 at the same rate while the right drive wheel 114R is driven forward at a lesser rate and the left drive wheel 114L is driven forward at a greater rate. The difference in the rate that each drive wheel 114R, 114L, 118F and 118B is driven relative to each other is in proportion to the difference in the turning radius of each particular drive wheel when a turn is made. When making a turn to the right, the drive wheels 118F/118B have a bigger turning radius than drive wheel 114R and have to be driven at a greater rate in order to travel a greater distance in the same amount of time. In addition, drive wheel 114L has an even bigger turning radius than drive wheels 118F/118B when making the turn to the right. To make a left forward turn, the steerable front drive wheel 118F is turned to the left and the back steerable drive wheel 118B is turned to the right. When the drive wheels 114R, 114L, 118F and 118B are driven, drive wheels 118F/118B are driven at the same rate while the left drive wheel 114L is driven forward at a lesser rate and the right drive wheel 114R is driven forward at a greater rate, with the radius of turn being in the opposite direction. A smaller turning radius is obtained by turning the steerable drive wheels 118F/118*b* at greater angles while a larger turning radius is obtained by turning steerable drive wheels 118F/118B at lesser angles.

To make a backward arched turn to the right, the steerable drive wheels 118F/118B are positioned as shown in FIG. 20 but the drive wheels 114R, 114L, 118F and 118B are driven in the backward direction toward the back B of robot 91. To make a backward arched turn to the left, the steerable drive wheels 118F/1118B are positioned in a similar manner as described for making a left forward turn, but the drive wheels 114R, 114L, 118F and 118B are driven in the backward direction. The rate of the rotation of drive wheels 114R, 114L, 118F and 118B relative to each other, as in forward arched turns, is proportional to the turning radius of each drive wheel.

Figure 21:
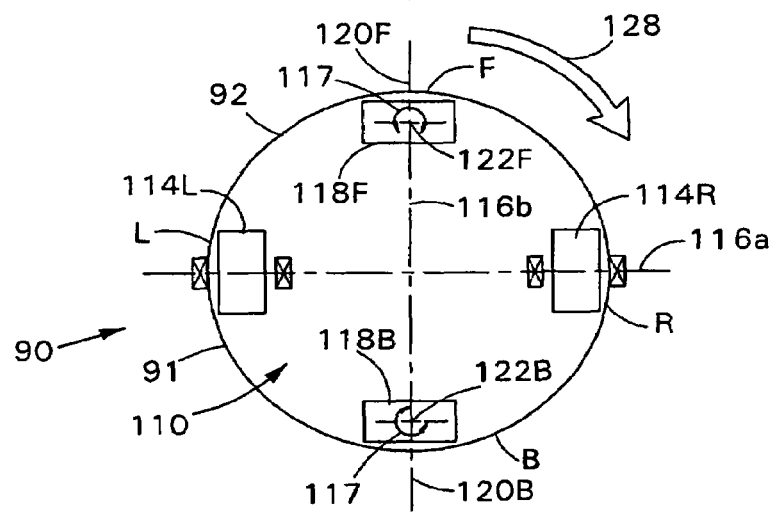

Referring to FIG. 21, robot 91 can be rotated by propulsion system 110 to the right or clockwise in the direction of arrow 128 while remaining in the same location. This is accomplished by turning the steerable drive wheels 118F/118B about axes 122F/122B to be perpendicular to drive wheels 114R/114L in order to have perpendicular directions of rotation. The drive wheels 114R, 114L, 118F and 118B are then driven in unison at the same rate, with drive wheel 114R being rotated towards the back B of robot 91, drive wheel 114L being rotated in the opposite direction towards the front F, drive wheel 118F being rotated in the direction towards the right side R of robot 91, and drive wheel 118B being rotated in the opposite direction towards the left side L. The robot 91 can be rotated a limited amount or can spin in place. In order to rotate in the counterclockwise direction or to the left, the drive wheels 114R, 114L, 118F and 118B are rotated in the opposite direction to that described for clockwise rotation.

The embodiment of the propulsion system 110 depicted in FIGS. 18–21 provides robot 91 and irradiation apparatus 90 with the ability to make tight radius turns as well as to rotate the robot 91 while remaining in a stationary location. Consequently, by linking together the motions shown in FIGS. 19–21 and described above, the irradiation apparatus 90 is able to maneuver within most any room 112, or around most any object 115, for positioning maneuvering arm 99 in the proper position to provide continuous irradiation coverage with electron beam generator 12. The cylindrical shape of the base 92 also maximizes the maneuverability of robot 91 as well as the ability to operate in areas with limited space. Although all the drive wheels 114R, 114L, 118F and 118B are preferably driven in order to obtain the best maneuverability, alternatively, in some embodiments, only drive wheels 114R/114L are driven. In other embodiments, only drive wheels 118F/118B are driven. In addition, various wheels 114R, 114L, 118F and 118B can be intermittently driven or intermittently serve as idler wheels. In embodiments where not all of the wheels are driven, the robot 91 typically has to move before being able to initiate a turn, while if all wheels are driven, no initial motion is required. As a result, the embodiments of propulsion system 110 which drive all the wheels 114R, 114L, 118F and 118B have increased maneuverability, which is desirable when maneuvering within a room 112 or around an object 115. Although the drive wheels 114R, 114L, 118F and 118B are preferably the same distance apart from each other as shown, alternatively, some of the drive wheels can be positioned closer together than others, depending upon the situation at hand.

Figure 22:
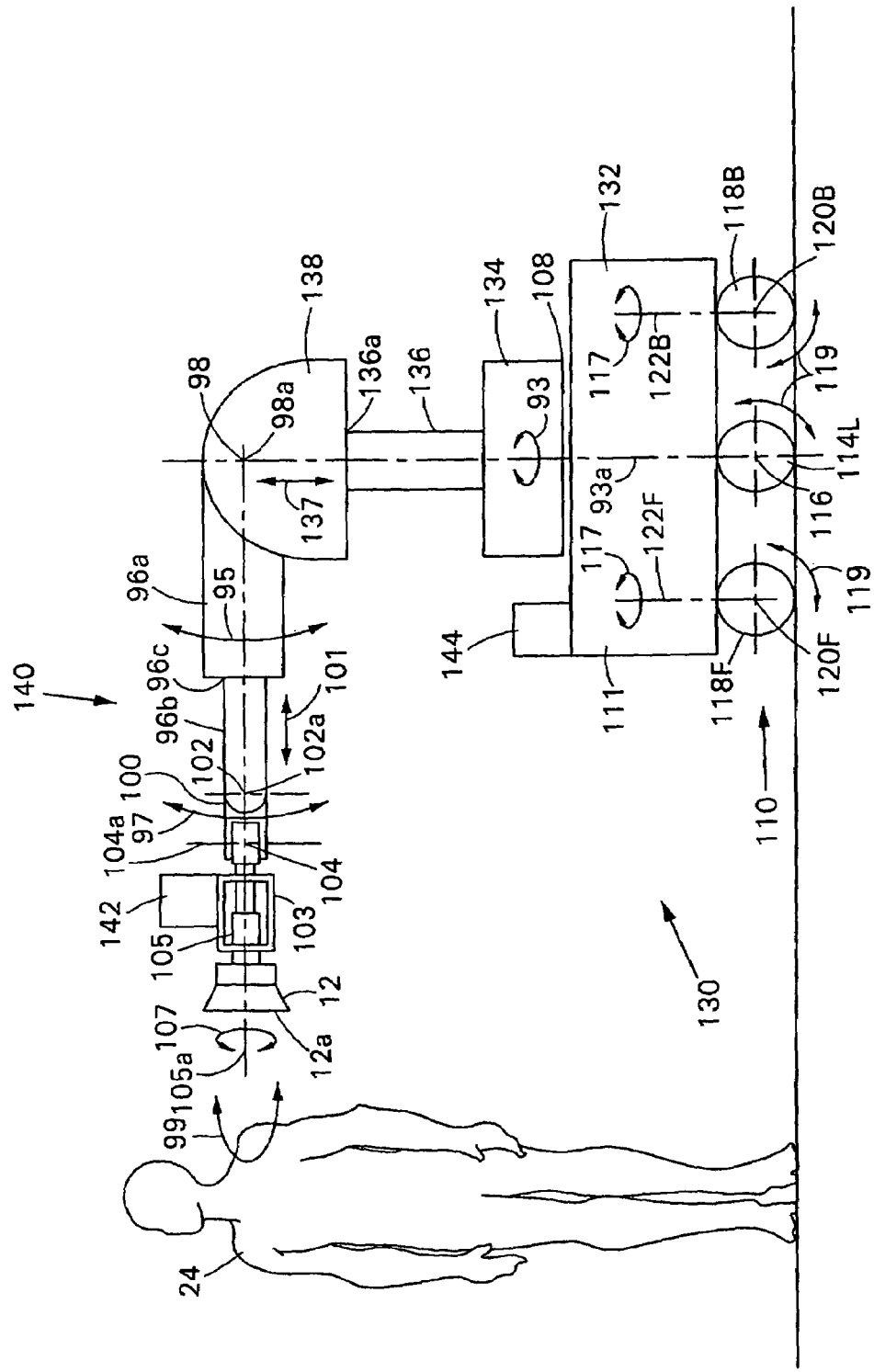
FIG. 22 is a side view of another mobile robotic irradiation apparatus in the present invention.

Referring to FIG. 22, mobile robotic irradiation apparatus 130 is another embodiment of the present invention which differs from irradiation apparatus 90 in that robot 111 has a turret 134 rotatably mounted to a base 132 about waist joint 108 with a vertical post 136 extending upwardly along axis 93a. A shoulder member 138 is slidably mounted to post 136 by a linear sliding joint 136a allowing vertical movement of shoulder member 138 up and down in the direction of arrows 137. Maneuverable arm 140 is rotatably mounted to shoulder member 138 at shoulder joint 98. Maneuverable arm 140 includes an upper arm member 96 having a first portion 96a and a second portion 96b. The second portion 96b is slidably mounted within and to the first portion 96a by a linear sliding joint 96c allowing linear extension and retraction of the second portion 96b in the direction of arrows 101. The two linear sliding joints 136a and 96c provide two additional degrees of movement than found in irradiation apparatus 90, allowing additional maneuverability. The joints of robot 111 can be driven by rotary drive motors such as described for robot 91. However, in some embodiments, the sliding joints 136a and 96c can be driven by linear motors.

In addition, irradiation apparatus 130 can include one or both of vision systems 142 and 144 shown located on base 132 and electron beam generator 12. The vision systems 142/144 can be employed for visually guiding the robot 111 and electron beam generator 12 while being moved and during the irradiation process. The vision systems 142/144 can also be employed for measuring a room 112 or object 115 to be irradiated for determining the manner in which irradiation is to be accomplished. The path at which the electron beam generator 12 is moved over the surfaces can be preprogrammed or can be continuously calculated. Alternatively, vision systems 142/144 can be employed for aiding in remotely controlling and operating irradiation apparatus 130 from a remote position. In some cases, non-vision sensing systems can also be included. Irradiation apparatus 90 can also be constructed with such features. Irradiation apparatus 130, as well as irradiation apparatus 90, can be employed for irradiating living creatures such as a human 24 as shown, as well as a room 112 or object 115. When irradiating living creatures, an irradiation or decontamination apparatus such as designated 10, 80 and 82 in FIGS. 1, 4, 8 and 9 can be employed. Gas supply and/or removal systems can be included as well as spacing devices or systems. For some applications, rotary and sliding joints can be added or omitted.

Figure 23:
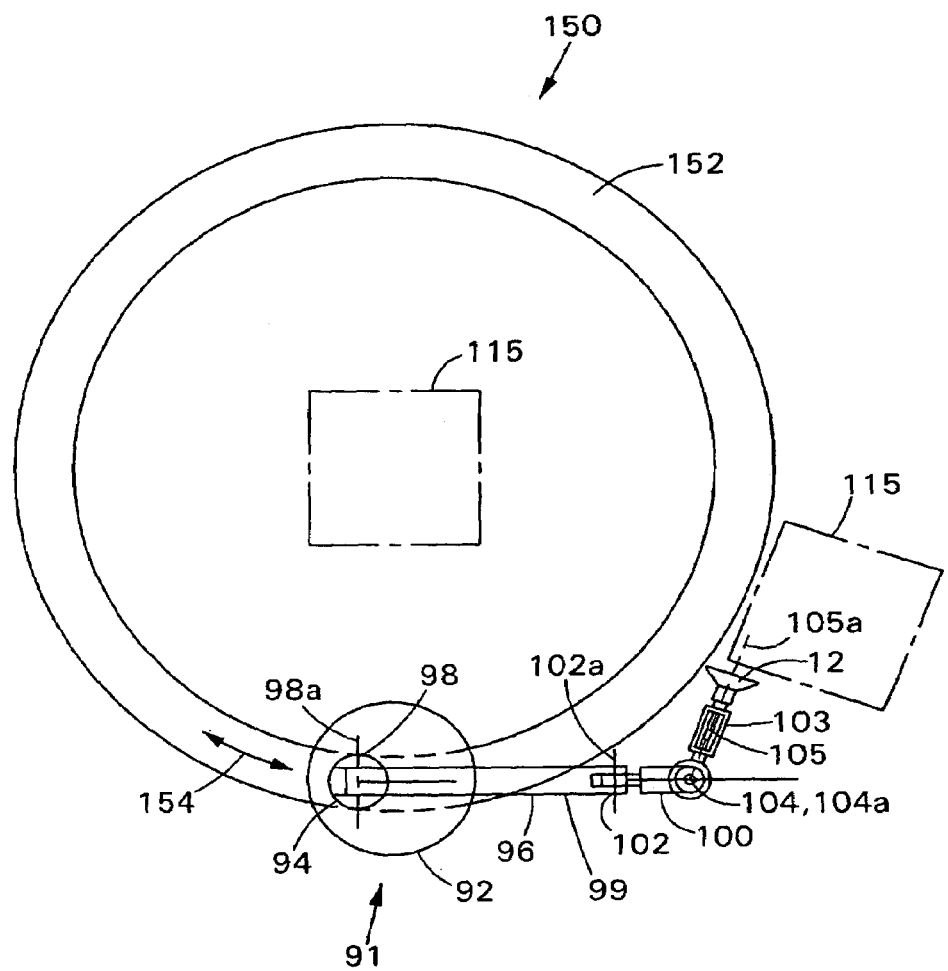
FIG. 23 is a side view of yet another mobile robotic irradiation apparatus in the present invention.

Referring to FIG. 23, mobile robotic irradiation apparatus 150 is another embodiment of the present invention which differs from irradiation apparatus 90 in that the mobile robot 91 does not have propulsion system 110 but instead is driven in a fixed path on a track 152 in the direction of arrows 154 with a simple two-directional drive or propulsion system. The track 152 can be circular as shown for moving robot 91 into position for irradiating surfaces with a beam 16 of electrons $e^-$ from electron beam generator 12, for example, an object 115, as shown. Surfaces outside of track 152 can also be irradiated, for example, an object 115. In another embodiment, the base 92 of mobile robot 91 can be fixed to track 152 with track 152 being movable and acting as the drive or propulsion system for moving robot 91 along a fixed path. Such a movable track 152 can be a rotary table. Although track 152 is shown to be circular, track 152 can be linear or have curved and linear portions, depending upon the situation at hand. In addition, although robot 91 is shown driven on track 152, alternatively, robot 111 can be substituted for robot 91. The track 152 can be positioned at ground or floor level, or be elevated such as overhead. When track 152 is overhead, robot 91 or 111 can be positioned to hang downwardly from track 152. Vision systems, spacing devices or systems, and gas supply and/or removal systems can be included depending upon the situation at hand.

While this invention has been particularly shown and described with references to preferred embodiments thereof, it will be understood by those skilled in the art that various changes in form and details may be made therein without departing from the scope of the invention encompassed by the appended claims.

For example, although propulsion system 110 has been shown with drive wheels, the wheels can be replaced with tractor treads for operation on uneven surfaces, such as outdoors. When employed outdoors, the present invention can irradiate ground surfaces including paved surfaces. In addition, although the electron beam generator 12 typically provides a wide beam 16, alternatively, a thin electron beam can be generated that is scanned back and forth. It is understood that features of the different embodiments described can be combined or omitted. Furthermore, although the mobile robotic irradiation apparatuses have been shown to maneuver one electron beam generator 12, it is understood that in some applications more than one electron beam generator 12 can be maneuvered.

What is claimed is:

1. An apparatus for irradiating surfaces comprising:
   an electron beam generator for generating a beam of electrons, the beam of electrons exiling the electron beam generator through an exit window; and
   a robotic device for moving the beam of electrons over the surfaces to irradiate selected regions of the surfaces, the robotic device including a robotic arm for maneuvering the electron beam generator, and a propulsion system for propelling the robotic device in a manner where the entire robotic device is capable of traveling to desired locations, the robotic device capable of controllably spacing the exit window of the electron beam generator a desired distance away from the surfaces as the electron beam generator is moved over the surfaces by both maneuvering by the robotic arm and by travel of the entire robotic device.

2. The apparatus of claim 1 in which the robotic device includes a horizontal rotary joint for swinging the robotic arm.

3. The apparatus of claim 2 in which the robotic arm comprises:
an upper arm member;
a rotary shoulder joint rotatably coupled to the upper arm member for raising and lowering the robotic arm;
a lower arm member rotatably coupled to the upper arm member by a rotary elbow joint, the elbow joint for raising and lowering the lower arm member relative to the upper arm member;
a bracket rotatably coupled to the lower arm member by a rotary wrist joint, the wrist joint for swinging the bracket from side to side; and
a rotary bracket joint rotatably coupling the electron beam generator to the bracket for rotating the electron beam generator.

4. The apparatus of claim 1 in which the propulsion system comprises:
a first pair of rotatable wheels rotatably fixed and spaced apart from each other along a first axis, the first pair of wheels being rotatably driven; and
a second pair of rotatable wheels spaced apart from each other along a second axis transverse to the first axis, the wheels of the second pair each being pivotably mounted and steerable.

5. The apparatus of claim 4 in which the second pair of wheels is rotatably driven.

6. The apparatus of claim 5 in which each wheel in the first and second pairs of rotatable wheels can be independently driven.

7. The apparatus of claim 1 in which the robotic device moves along a track.

8. The apparatus of claim 1 in which the robotic device is capable of continuously and actively spacing the exit window of the electron beam generator the desired distance away from the surfaces.

9. The apparatus of claim 8 in which the electron beam generator is hermetically sealed.

10. The apparatus of claim 1 in which irradiating the surfaces includes any of sterilization, decontamination, curing, destroying molecules and facilitating chemical reactions.

11. A method of irradiating surfaces comprising:
generating a beam of electrons with an electron beam generator, the beam of electrons exiting the electron beam generator through an exit window;
moving the beam of electrons over the surfaces with a robotic device to irradiate selected regions of the surfaces, the robotic device including a propulsion system for propelling the robotic device in a manner where the entire robotic device is capable of traveling to desired locations;
maneuvering the beam of electrons over the surfaces with a robotic arm; and
controllably spacing the exit window of the electron beam generator a desired distance away from the surfaces as the electron beam generator is moved over the surfaces by both maneuvering by the robotic arm and by travel of the entire robotic device.

12. The method of claim 11 further comprising swinging the robotic arm with a horizontal rotary joint.

13. The method of claim 11 further comprising:
raising and lowering the robotic arm with a rotary shoulder joint coupled to an upper arm member of the robotic arm;
raising and lowering a lower arm member of the robotic arm relative to the upper arm member by a rotary elbow joint rotatably coupling the lower arm member to the upper arm member;
swinging the electron beam generator from side to side with a rotary wrist joint rotatably coupling the lower arm member to a bracket housing the electron beam generator; and
rotating the electron beam generator with a rotary bracket joint rotatably coupling the electron beam generator to the bracket.

14. The method of claim 11 further comprising:
propelling the robotic device with a first pair of rotatable wheels rotatably fixed and spaced apart from each other along a first axis, the first pair of wheels being rotatably driven, and
steering the robotic device with a second pair of rotatable wheels spaced apart from each other along a second axis transverse to the first axis, the wheels of the second pair each being pivotably mounted.

15. The method of claim 14 further comprising rotatably driving the second pair of wheels.

16. The method of claim 15 further comprising independently driving each wheel in the first and second pairs of rotatable wheels.

17. The method of claim 11 further comprising moving the robotic device along a track.

18. The method of claim 11 further comprising continuously and actively spacing the exit window of the electron beam generator the desired distance away from the surfaces.

19. The method of claim 18 further comprising hermetically sealing the electron beam generator.

20. The method of claim 11 further comprising irradiating the surfaces for any of sterilization, decontamination, curing, destroying molecules and facilitating chemical reactions.

21. A method of forming an apparatus for irradiating surfaces comprising;
providing an electron beam generator for generating a beam of electrons, the beam of electrons exiting the electron beam generator through an exit window; and
arranging a robotic device relative to the electron beam generator for moving the beam of electrons over the surfaces to irradiate selected regions of the surfaces, the robotic device including a robotic arm for maneuvering the electron beam generator, and a propulsion system for propelling the robotic device in a manner where the entire robotic device is capable of traveling to desired locations, the robotic device capable of controllably spacing the exit window of the electron beam generator a desired distance away from the surfaces as the electron beam generator is moved over the surfaces by both maneuvering by the robotic arm and by travel of the entire robotic device.

* * * * *

UNITED STATES PATENT AND TRADEMARK OFFICE
CERTIFICATE OF CORRECTION

PATENT NO. : 7,183,563 B2 Page 1 of 1
APPLICATION NO. : 10/796796
DATED : February 27, 2007
INVENTOR(S) : Tzvi Avnery It is certified that error appears in the above-identified patent and that said Letters Patent is hereby corrected as shown below:

Column 14, line 60, delete "exiling" and insert --exiting--;

Column 16, line 41, delete "scaling" and insert --sealing--.

Signed and Sealed this

First Day of May, 2007

JON W. DUDAS
*Director of the United States Patent and Trademark Office*